United States Patent
Kawagishi

(10) Patent No.: US 9,916,425 B2
(45) Date of Patent: Mar. 13, 2018

(54) MEDICAL DIAGNOSIS SUPPORT DEVICE, MEDICAL DIAGNOSIS SUPPORT METHOD, AND INFORMATION PROCESSING METHOD

(71) Applicant: CANON KABUSHIKI KAISHA, Tokyo (JP)

(72) Inventor: Masami Kawagishi, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 319 days.

(21) Appl. No.: 14/012,825

(22) Filed: Aug. 28, 2013

(65) Prior Publication Data

US 2014/0067412 A1    Mar. 6, 2014

(30) Foreign Application Priority Data

Aug. 30, 2012   (JP) .................................. 2012-189932

(51) Int. Cl.
   *G06F 19/24* (2011.01)
   *G06F 19/00* (2018.01)

(52) U.S. Cl.
   CPC ........ *G06F 19/345* (2013.01); *G06F 19/3443* (2013.01); *G06F 19/321* (2013.01)

(58) Field of Classification Search
   CPC ... G06F 19/3443; G06F 19/345; G06F 19/321
   See application file for complete search history.

(56) References Cited

U.S. PATENT DOCUMENTS

| | | | | |
|---|---|---|---|---|
| 8,949,171 | B2* | 2/2015 | Kawagishi | G06F 19/321 706/52 |
| 9,117,009 | B2* | 8/2015 | Iizuka | G06F 19/3487 |
| 9,361,580 | B2* | 6/2016 | Kawagishi | G06N 5/02 |
| 9,384,326 | B2* | 7/2016 | Kawagishi | G06Q 50/22 |
| 9,436,915 | B2* | 9/2016 | Kawagishi | G06F 19/321 |
| 9,519,866 | B2* | 12/2016 | Kawagishi | G06F 19/3443 |
| 9,715,657 | B2* | 7/2017 | Kawagishi | G06F 19/345 |
| 9,734,299 | B2* | 8/2017 | Yakami | G06F 19/345 |
| 9,734,300 | B2* | 8/2017 | Kawagishi | G06F 19/345 |
| 2008/0294692 | A1* | 11/2008 | Angell | G06F 19/3443 |

(Continued)

FOREIGN PATENT DOCUMENTS

JP   2010-200840 A   9/2010

*Primary Examiner* — Minnah L Seoh
(74) *Attorney, Agent, or Firm* — Canon USA Inc., IP Division

(57) ABSTRACT

The present invention provides a diagnosis support system for presenting medical support information on a case. The system includes an inference unit, an acquisition unit, a determination unit, and a display control unit. The inference unit identifies a diagnostic name of the case and obtains its inferred probability in accordance with medical information including a set having a plurality of elements. The acquisition unit acquires an influence of each of first subsets contained in the set and an influence of each of second subsets contained in each of the first subsets upon the inferred probability. The determination unit determines, in accordance with the influence of each of the first subsets and the influence of each of the second subsets, a subset of the plurality of elements that is to be displayed. The display control unit allows a display unit to display the identified diagnostic name and the determined subset.

18 Claims, 8 Drawing Sheets

| $S_{jk}$ | $I(D_r|S_{jk})$ [%] |
|---|---|
| $S_{12}$ | 10.4 |
| $S_{21}$ | 7.13 |
| $S_{33}$ | -2.16 |
| $S_{43}$ | 2.51 |
| | |
| $S_{11}$ | 1.09 |
| | |
| $S_{m2}$ | 8.23 |

FIRST INFLUENCE

| $E_{2x}(E_{Nx})$ | $I(D_r|E_{2x})$ [%] | $E_{2x}$ | $I(D_r|E_{2x})$ [%] |
|---|---|---|---|
| $\{S_{12}, S_{21}\}$ | 9.55 | | ... |
| $\{S_{12}, S_{33}\}$ | 6.10 | | |
| ... | | $\{S_{43}, S_{11}\}$ | 12.7 |
| $\{S_{21}, S_{33}\}$ | 4.07 | | |
| ... | | | ... |
| $\{S_{21}, S_{11}\}$ | 5.05 | | |
| ... | | | |
| $\{S_{33}, S_{m2}\}$ | 3.45 | $\{I_{m-1}, I_m\}$ | 6.06 |

SECOND (N = 2) INFLUENCE

(56) References Cited

U.S. PATENT DOCUMENTS

| | | | |
|---|---|---|---|
| 2010/0278405 A1* | 11/2010 | Kakadiaris | G06F 19/3431 382/131 |
| 2010/0332441 A1* | 12/2010 | Kawagishi | G06F 19/321 706/52 |
| 2012/0254101 A1* | 10/2012 | Kawagishi | G06F 19/3443 706/52 |
| 2014/0067412 A1* | 3/2014 | Kawagishi | G06F 19/321 705/2 |
| 2015/0023579 A1* | 1/2015 | Fujimoto | G06T 7/0014 382/132 |

\* cited by examiner

FIG. 5

| j | $I_j$ (FINDING NAME) | jk | $S_{jk}$ (STATE NAME) |
|---|---|---|---|
| 1 | SHAPE | 11 | SPHERICAL |
| | | 12 | LOBULAR |
| | | 13 | IRREGULAR |
| 2 | NOTCH | 21 | SIGNIFICANT |
| | | 22 | MEDIUM |
| | | 23 | INSIGNIFICANT |
| | | 24 | ABSENT |
| 3 | RADIAL | 31 | SIGNIFICANT |
| | | 32 | MEDIUM |
| | | 33 | INSIGNIFICANT |
| | | 34 | ABSENT |
| 4 | TRANSLUCENCY | 41 | PRESENT |
| | | 42 | SUSPECTED |
| | | 43 | ABSENT |
| ... | | | |
| l | INVOLVEMENT (BRONCHIAL TUBE) | l1 | PRESENT |
| | | l2 | SUSPECTED |
| | | l3 | ABSENT |
| ... | | | |
| m | PAST HISTORY | m1 | PRESENT |
| | | m2 | ABSENT |

FIG. 6

| $S_{jk}$ | $I(D_r|S_{jk})$ [%] |
|---|---|
| $S_{12}$ | 10.4 |
| $S_{21}$ | 7.13 |
| $S_{33}$ | -2.16 |
| $S_{43}$ | 2.51 |
| $S_{I1}$ | 1.09 |
| $S_{m2}$ | 8.23 |

FIRST INFLUENCE

| $E_{2x}(E_{Nx})$ | $I(D_r|E_{2x})$ [%] | $E_{2x}$ | $I(D_r|E_{2x})$ [%] |
|---|---|---|---|
| $\{S_{12}, S_{21}\}$ | 9.55 | | |
| $\{S_{12}, S_{33}\}$ | 6.10 | ⋮ | ⋮ |
| $\{S_{21}, S_{33}\}$ | 4.07 | $\{S_{43}, S_{I1}\}$ | 12.7 |
| $\{S_{21}, S_{I1}\}$ | 5.05 | | |
| ⋮ | ⋮ | ⋮ | ⋮ |
| $\{S_{33}, S_{m2}\}$ | 3.45 | $\{I_{m-1}, I_m\}$ | 6.06 |

SECOND (N = 2) INFLUENCE

FIG. 8

| $S_{jk}$ | $I(D_r\|S_{jk})$ [%] |
|---|---|
| $S_{12}$ | 10.4 |
| $S_{21}$ | 7.13 |
| $S_{33}$ | -2.16 |
| $S_{43}$ | 2.51 |
| ⋮ | ⋮ |
| $S_{11}$ | 1.09 |
| $S_{m2}$ | 8.23 |

FIRST INFLUENCE

| $E_{2x}(E_{Nx})$ | $I(D_r\|E_{2x})$ [%] | $E_{2x}$ | $I(D_r\|E_{2x})$ [%] |
|---|---|---|---|
| $\{S_{12}, S_{21}\}$ | 0.891 | | |
| $\{S_{12}, S_{33}\}$ | -1.55 | ⋮ | ⋮ |
| ⋮ | -1.03 | $\{S_{43}, S_{11}\}$ | 15.3 |
| $\{S_{21}, S_{33}\}$ | ⋮ | | |
| $\{S_{21}, S_{11}\}$ | -0.0728 | | |
| $\{S_{33}, S_{m2}\}$ | -3.06 | $\{I_{m-1}, I_m\}$ | 0.278 |

SECOND (N = 2) INFLUENCE

MEDICAL DIAGNOSIS SUPPORT DEVICE, MEDICAL DIAGNOSIS SUPPORT METHOD, AND INFORMATION PROCESSING METHOD

BACKGROUND OF THE INVENTION

Field of the Invention

The present disclosure relates to a technique of presenting information for supporting a medical diagnosis.

Description of the Related Art

In the medical field, diagnostic imaging is performed where doctors interpret medical images obtained through an imaging device, such as an X-ray CT scanner and an MRI, to make a diagnosis. To perform the diagnostic imaging in response to a request for an interpretation from a doctor in charge, a doctor comprehensively evaluates findings (hereinafter referred to as "image findings") obtained from the images, various measurements, and the like to identify symptoms of a lesion in the image. The doctor, then, organizes reasons for arriving at a diagnosis into an interpretation report, with the image findings and the measurements cited, for the requesting doctor in charge.

In recent years, diagnosis support apparatuses have been developed in order to support such diagnostic imaging. For example, Japanese Patent Application Laid-Open No. 2010-200840 discloses a technique of presenting a result of inference based on input information and of presenting negative information and affirmative information about the result of the inference.

SUMMARY OF THE INVENTION

According to some embodiments of the present invention, there is provided a diagnosis support system for presenting medical support information on a case, and the system includes an inference unit configured to identify a diagnostic name of the case and obtaining an inferred probability of the diagnostic name in accordance with medical information including a set having a plurality of elements, an acquisition unit configured to acquire an influence, upon the inferred probability, of each of first subsets contained in the set, and an influence, upon the inferred probability, of each of second subsets contained in each of the first subsets, a determination unit configured to determine, in accordance with the influence of each of the first subsets and the influence of each of the second subsets, a subset of the plurality of elements that is to be displayed, and a display control unit configured to allow a display unit to display the identified diagnostic name and the determined subset.

Further features of the present invention will become apparent from the following description of exemplary embodiments (with reference to the attached drawings).

BRIEF DESCRIPTION OF THE DRAWINGS

FIG. 5 is a diagram of examples of input information.

FIG. 6 is a diagram of examples of first influences and Nth influences in a first embodiment.

FIG. 8 is a diagram of examples of first influences and Nth influences in a second embodiment.

DESCRIPTION OF THE EMBODIMENTS

Some preferred embodiments of the present invention will now be described. Note that the embodiments to be described herein are presented merely as examples of the application of the present invention and are not intended to limit the present invention.

A first embodiment of the present invention will now be described. A medical diagnosis support device according to the first embodiment of the present invention acquires medical information relevant to a case to be diagnosed as input information to perform diagnosis support for the case. For example, the medical diagnosis support device according to the present embodiment acquires a plurality of image findings on an abnormal shadow of a lung, past medical records, and tumor marker values, which are clinical information, as the input information. The medical diagnosis support device according to the present embodiment, then, infers an abnormality type (diagnostic name) of the abnormal shadow from the acquired input information to present diagnosis support information based on a result of the inference. Of course, the target of the inference is not limited by this, and any diagnostic name, interpretation finding, clinical information, or the like provided herein is an example for describing a process of the medical diagnosis support device according to the present embodiment.

Figure 1:
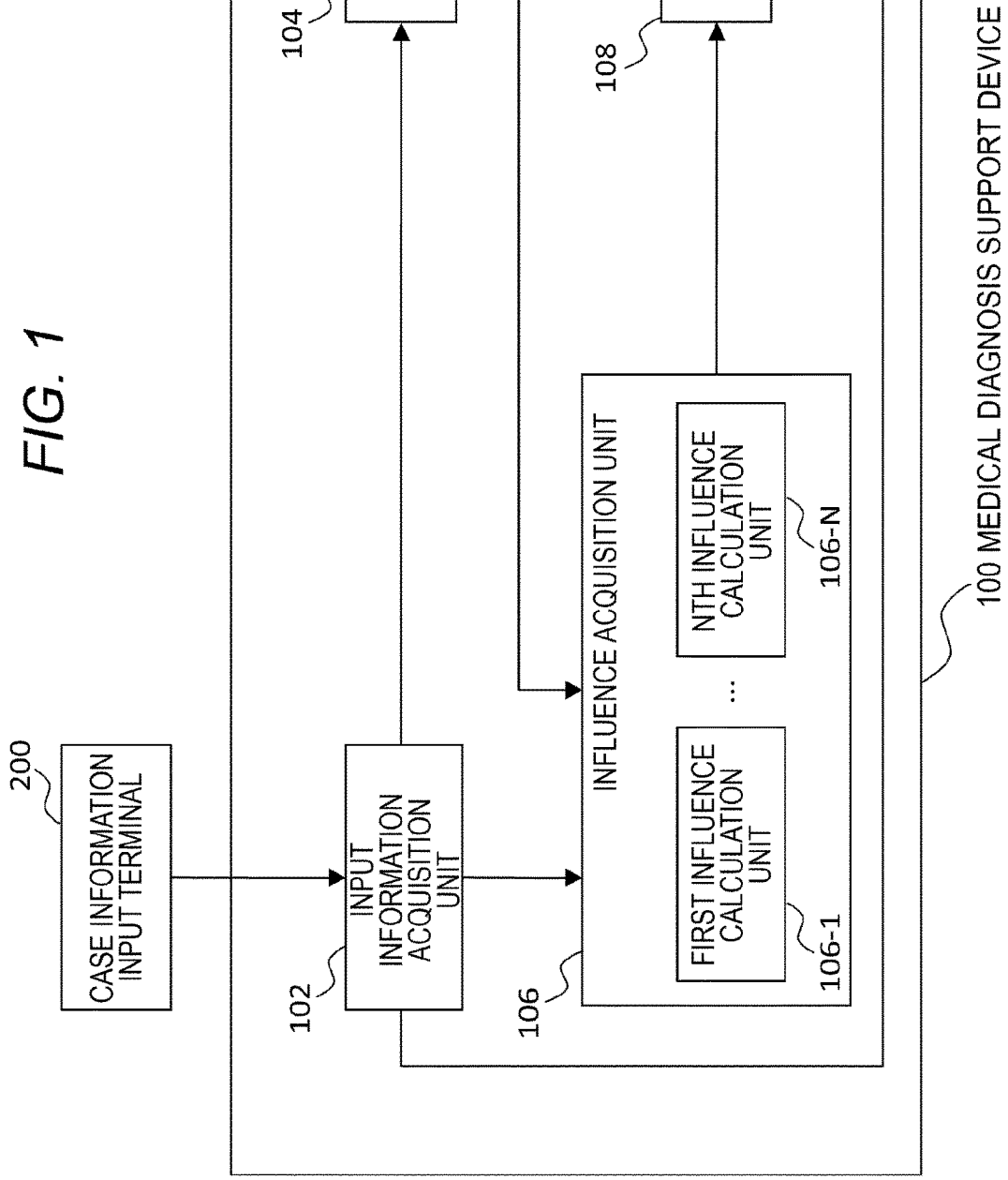
FIG. 1 is a diagram of a configuration of a medical diagnosis support device according to some embodiments of the present invention.

FIG. 1 is a diagram of a functional configuration of the medical diagnosis support device according to the first embodiment. As illustrated in FIG. 1, a medical diagnosis support device 100 according to the first embodiment is connected to a case information input terminal 200. The case information input terminal 200 acquires, from a server not illustrated, the medical information (medical image data, an electronic medical record, and the like) relevant to the abnormal lung shadow relating to the case to be diagnosed. Alternatively, the case information input terminal 200 may be connected to an external storage device (for example, an FDD, an HDD, a CD drive, a DVD drive, an MO drive, or a ZIP drive) to acquire the medical information from the external storage device. The case information input terminal 200 allows a monitor to display the medical information such that a user (the doctor) can perform the interpretation. The case information input terminal 200 also acquires the image findings, the past medical record, and the clinical information as the input information in response to an operation by the user. The image findings are input in response to the operation of a mouse, a keyboard, or the like by the user. To achieve this processing, the case information input terminal 200 is provided with, for example, a function for using an interpretation finding input support process of a template-type to allow selection of an interpretation finding through a GUI. The case information input terminal 200 sends through a LAN, etc. to the medical diagnosis support device 100 the input information and data (representative image data and the like) accompanying the input information in accordance with the operation of the user.

The medical diagnosis support device 100 includes an input information acquisition unit 102, an inference unit 104, an influence acquisition unit 106, and a presentation unit 108. The input information acquisition unit 102 acquires from the case information input terminal 200 the input information and the data accompanying the input information, and outputs the information and the data to the inference unit 104, the influence acquisition unit 106, and the presentation unit 108. The inference unit 104 performs the inference based on the input information on the abnormal lung shadow to be diagnosed, and calculates a probability (a result of the inference) of each diagnostic name for the abnormal shadow. The calculated result of the inference is output to the influence acquisition unit 106 and the presentation unit 108.

The influence acquisition unit 106 is provided with N (N>1) influence calculation units (where N represents the number of the units), which are a first influence calculation unit 106-1, . . . , and an Nth influence calculation unit 106-N. The influence acquisition unit 106 acquires an influence calculated by each of the first to Nth influence calculation units 106-1 to 106-N by using the input information and the result of the inference calculated by the inference unit 104, and outputs the influences to the presentation unit 108.

The presentation unit 108 generates and displays information to be presented to the user. Specifically, the presentation unit 108 generates the information to be presented to the user on the basis of the input information and the data accompanying the input information, the result of the inference calculated by the inference unit 104, and the influences calculated by the influence acquisition unit 106.

Figure 2:
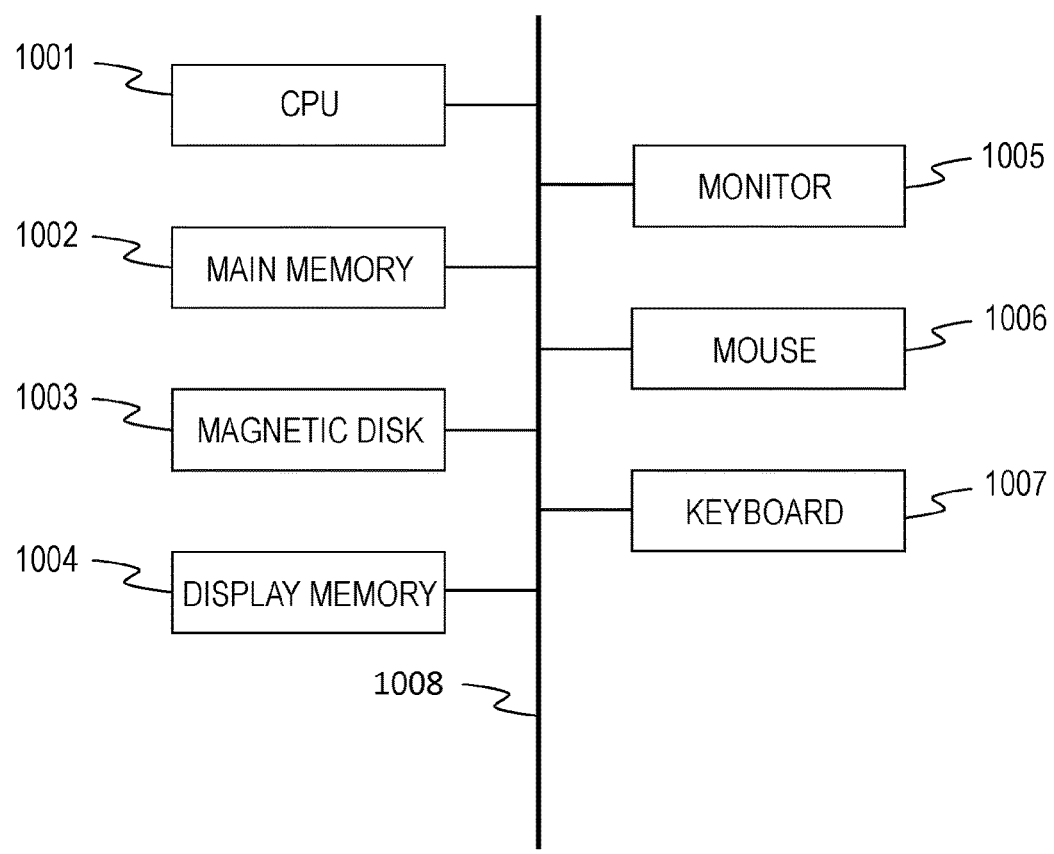
FIG. 2 is a diagram of a hardware configuration of the medical diagnosis support device according to the embodiments of the present invention.

FIG. 2 is a diagram of a hardware configuration of the medical diagnosis support device 100 according to the present embodiment. In FIG. 2, a CPU 1001 controls an operation of each component of the medical diagnosis support device 100. A main memory 1002 stores a program to be executed by the CPU 1001 and provides a workspace for the CPU 1001 to execute the program. A magnetic disk 1003 stores an operating system (OS), a device drive for a peripheral, and various types of application software including a program for performing processing to be described hereinafter. A display memory 1004 temporarily stores data for display. A monitor 1005 is, for example, a CRT monitor or a liquid crystal monitor, and displays an image, a text, and the like based on the data from the display memory 1004. A mouse 1006 and a keyboard 1007 input information of pointing by the user and a text, etc., respectively. The components described above are connected by a common bus 1008 such that mutual communication is possible.

Note that the CPU 1001 reads a desired program from the main memory and executes the program to achieve the configuration of the input information acquisition unit 102, the inference unit 104, the influence acquisition unit 106, and the presentation unit 108 illustrated in FIG. 1. In addition, at least part of configuration of the medical diagnosis support device 100 illustrated in FIG. 1 may be achieved with an independent device.

Figure 3:
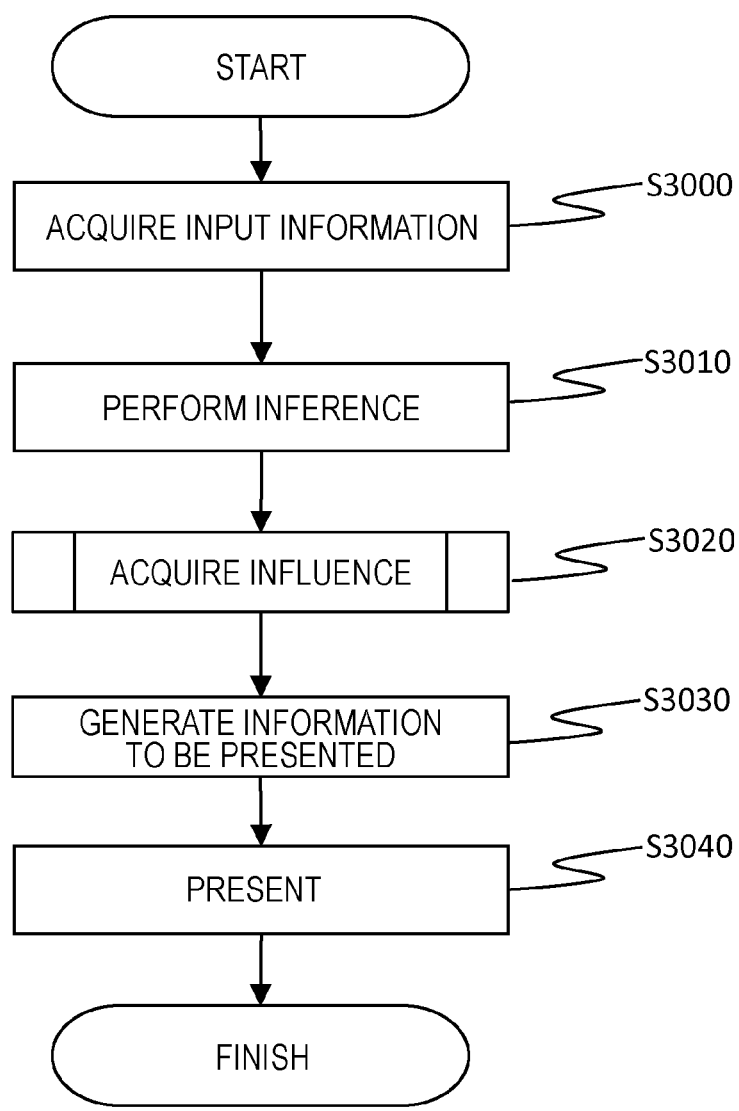
FIG. 3 is a flowchart of a process of the medical diagnosis support device according to the embodiments of the present invention.

With reference to FIGS. 3 and 5, processing of the medical diagnosis support device 100 according to the present embodiment will now be described. The description herein assumes that the names of the image findings and the clinical information are represented by $I_j$ (j=1 to m), so that m types of the names of the image findings and the clinical information $I_1$ to $I_m$ (where m represents the number of types) are handled. Also, k states that $I_j$ can possibly assume are denoted as $S_{jk}$ (where k represents the number of states). The range of k takes various values depending on $I_j$.

In the present embodiment, the image findings and the clinical information can be acquired as the input information, and furthermore, the image findings and the clinical information can each assume states as illustrated in FIG. 5.

For example, the "shape" denoted as represents a shape of the abnormal shadow, and can assume three states, namely "spherical" denoted as $S_{11}$, "lobular" denoted as $S_{12}$, and "irregular" denoted as $S_{13}$. The "notch" denoted as $I_2$ represents a degree of notch in the abnormal shadow. The "involvement (bronchial tube)" denoted as $I_1$ represents whether involvement of the bronchial tube is present in the abnormal shadow. Also, the "past history" denoted as $I_m$ represents whether or not there is past history of a disease.

A set of $S_{jk}$ is denoted as E hereinafter. Note that one E does not include more than one state $S_{jk}$ of one $I_j$ concurrently. For example, where $I_1$ can assume $S_{11}$, $S_{12}$, or $S_{13}$, and $I_2$ can assume $S_{21}$, $S_{22}$, $S_{23}$, or $S_{24}$, the expression E=[$S_{11}$, $S_{21}$] is possible, but the expression E={$S_{11}$, $S_{12}$} is not possible. This is because one interpretation finding and one piece of clinical information each assume only one state at a time. In the present embodiment, the input information is denoted as $E_f$. Also, the diagnostic name is denoted as D hereinafter. In the present embodiment, the diagnostic name assumes three values, namely, primary lung cancer, metastasis of a cancer to the lung, and other, which are denoted as $D_1$, $D_2$, and $D_3$, respectively. Given that a set E is provided, the probability (the result of the inference) of the diagnostic name $D_r$ (r=1, 2, 3) is denoted as P($D_r$|E). Similarly, given that $S_{jk}$ is provided, the probability (the result of the inference) of $D_r$ is denoted as P($D_r$|$S_{jk}$). Given that $E_f$ has N components (where N represents the number of components), a subset of $E_f$ is denoted as $E_{Nx}$, and the influence of $E_{Nx}$ upon the diagnostic name $D_r$ is denoted as I($D_r$|$E_{Nx}$). Similarly, the influence of $S_{jk}$ upon the diagnostic name $D_r$ is denoted as I($D_r$|$S_{jk}$). The above-mentioned $E_{Nx}$ may be also referred to as partial information N hereinafter.

In step S3000, the input information acquisition unit 102 acquires the input information relevant to the abnormal lung shadow and the data accompanying the input information. For example, the image findings and the tumor marker values acquired as the input information include $I_1$ "shape" being $S_{12}$ "lobular", $I_2$ "notch" being $S_{21}$ "significant", . . . , $I_l$ "involvement (bronchial tube)" being $S_{11}$ "present", . . . , and $I_m$ "past history" being $S_{m2}$ "absent". In this case, the set $E_f$ of $S_{jk}$ is described as $E_f$=[$S_{12}$, $S_{21}$, . . . , $S_{11}$, . . . , $S_{m2}$].

In step S3010, the inference unit 104 infers the probability (the result of the inference) of each diagnostic name for the abnormal shadow from the input information (i.e. $E_f$) acquired in step S3000. As inference means for this, various existing inference methodologies, such as a Bayesian network, a neural network, and a support vector machine, may be used. In the present embodiment, a Bayesian network is used as the inference methodology. A Bayesian network is an inference model employing a conditional probability, and is capable of acquiring the probability of each diagnostic name, given that the input information has been input (the probability that the case is to fall under each diagnostic name, in other words, the posterior probability). In the present embodiment, the probability of each of the diagnostic names $D_1$, $D_2$, and $D_3$ for the abnormal shadow is acquired.

In step S3020, the influence acquisition unit 106 uses the input information acquired in step S3000 and the result of the inference acquired in step S3010 to acquire the influence.

Figure 4:
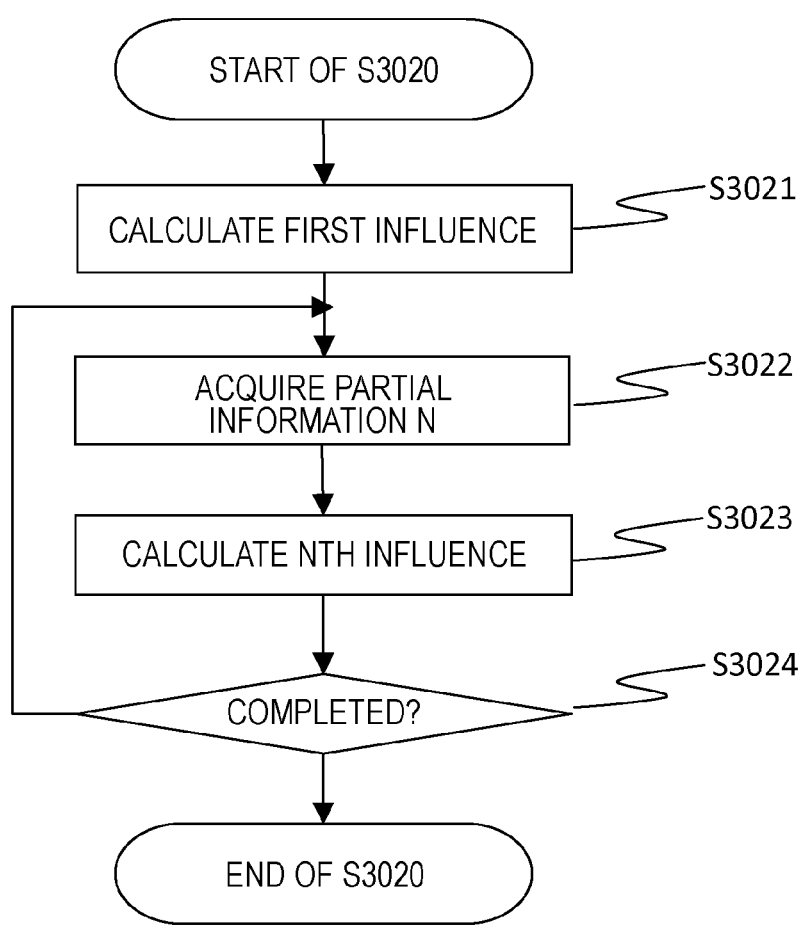
FIG. 4 is a flowchart of step S3020 in FIG. 3 in detail.

With reference to FIG. 4, step S3020 will now be described in detail. In step S3021, the first influence calculation unit 106-1 calculates a first influence of each component (i.e. $S_{jk}$) of the input information. In the present embodiment, the first influence calculation unit 106-1 uses a difference between the probability (i.e. the prior probability) of each diagnostic name with no input information provided and the probability with $S_{jk}$ alone input in order to calculate the first influence. For example, the first influence calculation unit 106-1 calculates the influence $I(D_r|S_{jk})$ of $S_{jk}$ upon the diagnostic name $D_r$ by using the expression described below, where $P(D_r)$ is the prior probability of $D_r$.

$$I(D_r|S_{jk}) = P(D_r|S_{jk}) - P(D_r) \quad \text{[Expression 1]}$$

If $I(D_r|S_{jk})$ is positive, that is, if the posterior probability with $S_{jk}$ alone input is larger than the prior probability, $S_{jk}$ has an affirmative influence upon $D_r$. Conversely, if $I(D_r|S_{jk})$ is negative, that is, if the posterior probability with $S_{jk}$ alone input is smaller than the prior probability, $S_{jk}$ has a negative influence upon $D_r$. Note that the calculation method described above for the influence is merely an example, and the present invention is not limited by this example.

In step S3022, the influence acquisition unit 106 acquires at least one piece of the partial information N. For example, if N=2 in the example described above where $E_f = [S_{12}, S_{21}, \ldots, S_{11}, \ldots, S_{m2}]$, then, pieces of the partial information N, such as $\{S_{12}, S_{21}\}$, $[S_{12}, S_{11}]$, and $[S_{21}, S_{m2}]$, are acquired. These acquired pieces of the partial information N correspond to $E_{Nx}$ described above. In the present embodiment, all pieces of the partial information N are acquired. For example, if the number of elements of $E_f$ is M (where M>=N), the number of pieces of the partial information N to be acquired $E_{Nx}$ is $_MC_N$.

In step S3023, the Nth influence calculation unit 106-N calculates an Nth influence for each piece of the partial information N (i.e. $E_{Nx}$). The Nth influence is calculated by using a difference between the prior probability of each diagnostic name and the probability with $E_{Nx}$ alone input, and by using the number N of components of the partial information N. For example, the influence $I(D_r|E_{Nx})$ of $E_{Nx}$ upon the diagnostic name $D_r$ is calculated with the expression described below.

$$I(D_r | E_{NX}) = \frac{P(D_r | E_{NX}) - P(D_r)}{\sqrt{N}} \quad \text{[Expression 2]}$$

Similarly to the description above, if $I(D_r|E_{Nx})$ is positive, $E_{Nx}$ has an affirmative influence upon $D_r$. Conversely, if $I(D_r|E_{Nx})$ is negative, $E_{Nx}$ has a negative influence upon $D_r$. Note that the calculation method described above for the influence is merely an example, and the present invention is not limited by this example.

In step S3024, the influence acquisition unit 106 determines whether or not the processing of step S3020 has been completed. If the processing of step S3020 has been completed, the processing moves on to step S3030. Conversely, if the processing of step S3020 has not been completed, the influence acquisition unit 106 updates N to a value not set yet, and the processing reverts to step S3022. The present embodiment considers an example of N=2 alone. That is, the processing of step S3022 to S3023 is performed once, and then the processing moves on to step S3030.

In step S3030, the presentation unit 108 generates and displays the information to be presented to the user. Specifically, the information to be presented to the user is generated on the basis of the input information and the data accompanying the input information acquired in step S3000, the result of the inference calculated in step S3010, and the influences acquired in step S3020. In the present embodiment, the influences acquired in step S3020, namely, the first influences to the Nth influences, are brought together, and information of largest influences by the number of influences specified in descending order is presented. Here, if the influence of at least one proper subset, which includes at least one component, of one piece of the partial information N is larger than the influence of the piece of the partial information N, the influence of the piece of the partial information N is not presented (the proper subset being a subset of a piece of the partial information N, and not including the piece of the partial information N itself). Note that a component or a piece of the partial information N presented through this processing equates to an inference reason.

With reference to FIG. 6, the processing described above will now be described in detail. FIG. 6 is a diagram of the first influences and second influences acquired through the processing of step S3020. In the present embodiment, three pieces of information are provided as inference reasons. The information of $\{S_{43}, S_{11}\}$, which has the largest influence, is presented unconditionally. The information of $[S_{12}]$, which has the next largest influence, is presented, because $[S_{12}]$ does not include a proper subset with one or more components. The information of $\{S_{12}, S_{21}\}$, which has the next largest influence, is not presented, because the influence of $\{S_{12}, S_{21}\}$ is smaller than the influence of its proper subset, $\{S_{12}\}$. The information of $\{S_{m2}\}$, which has the next largest influence, is presented, because $\{S_{m2}\}$ does not include a proper subset with one or more component. Accordingly, the information to be presented in conclusion is $\{S_{43}, S_{11}\}$, $\{S_{12}\}$, and $\{S_{m2}\}$.

Figure 7:
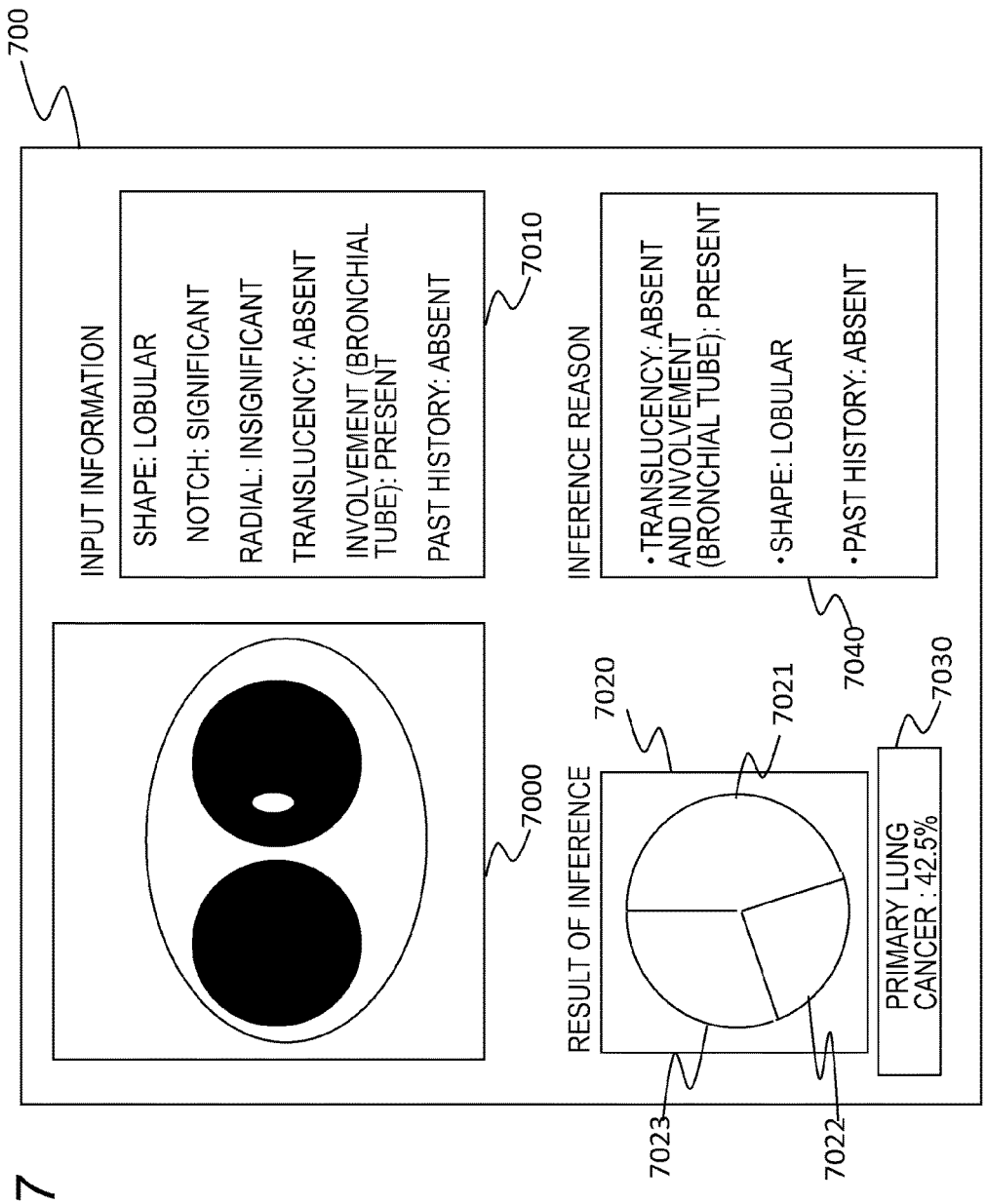
FIG. 7 is a diagram of an example of presented information displayed on the monitor.

FIG. 7 is a diagram of an example of presented information displayed on the monitor 1005. Presented information 700 includes input information 7010 relevant to the abnormal lung shadow and the data accompanying the input information (representative image data of the abnormal lung shadow) 7000 acquired in step S3000. In addition, the presented information 700 includes a result of inference 7020 obtained in step S3010. In the example illustrated in FIG. 7, an inferred probability 7021 of the primary lung cancer, an inferred probability 7022 of the metastasis of a cancer to the lung, and an inferred probability 7023 of other in the result of the inference are displayed in a pie chart as the result of the inference 7020. The presented information 700 also includes a diagnostic name (primary lung cancer in the example of FIG. 7), which has obtained the highest inferred probability among the diagnostic names in the result of the inference, and its probability (the inferred probability of the primary lung cancer in the example of FIG. 7) 7030. In addition, the presented information 700 includes information that is presented through step S3030 (the inference reason) 7040.

According to the present embodiment, the influence of an instance with more than one component (the partial information N) is lightened through the consideration of the number of components of the partial information. Furthermore, during the consideration of the partial information N, if the influence of at least one proper subset of one piece of the partial information N is larger than the influence of the piece of the partial information N, the influence of the piece of the partial information N is not presented. As a result, an instance of an influence simply added up due to each component of one piece of the partial information N and an instance of an influence increased because some components are combined are distinguished, thereby allowing a reduction of the presentation of the simple addition. Hence, more appropriate information that has affected the derivation of the result of the inference can be presented to the doctor.

A second embodiment of the present invention will now be described. In the second embodiment, during the consideration of the partial information N, attention is directed to components of the partial information N to calculate the influence. Note that the functional configuration of the medical diagnosis support device according to the second embodiment is similar to that of the configuration illustrated in FIG. 1. Accordingly, the description hereinafter also uses the reference figures in FIG. 1. The processing of a medical diagnosis support device 100 according to the second embodiment is similar to that illustrated in FIGS. 3 and 4, except for part of the processing of step S3020. Specifically, the processing performed in step S3023 is different from that of the first embodiment. The medical diagnosis support device 100 according to the second embodiment will now be described with main focus on differences from the first embodiment.

In step S3023 of the second embodiment, an Nth influence calculation unit 106-N uses first influences calculated in step S3021 to calculate an Nth influence of each piece of the partial information $N(E_{Nx})$. In the present embodiment, the Nth influence is calculated by using a difference between the prior probability of each diagnostic name and the probability with $E_{Nx}$ alone input, and by using the first influence of each component $S_{jk}$ of $E_{Nx}$. The influence $I(D_r|E_{Nx})$ of $E_{Nx}$ upon the diagnostic name $D_r$ is calculated with the expression described below.

$$I(D_r \mid E_{NX}) = \{P(D_r \mid E_{NX}) - P(D_r)\} - f(E_{NX}) \quad \text{[Expression 3]}$$

$$f(E_{NX}) = \begin{cases} \sqrt{f_p(E_{NX}) - f_m(E_{NX})} & \text{if } f_p(E_{NX}) \geq f_m(E_{NX}) \\ -\sqrt{f_m(E_{NX}) - f_p(E_{NX})} & \text{if } f_p(E_{NX}) < f_m(E_{NX}) \end{cases}$$

$$f_p(E_{NX}) = \sum_{S_{jk} \in E_{NX}, I(D_r|S_{jk}) \geq 0} I(D_r \mid S_{jk})^2$$

$$f_m(E_{NX}) = \sum_{S_{jk} \in E_{NX}, I(D_r|S_{jk}) < 0} I(D_r \mid S_{jk})^2$$

Similarly to the first embodiment, if $I(D_r|E_{Nx})$ is positive, $E_{Nx}$ has an affirmative influence upon $D_r$. Conversely, if $I(D_r|E_{Nx})$ is negative, $E_{Nx}$ has a negative influence upon $D_r$. Note that the calculation method described above for the influence is merely an example, and the present invention is not limited by this example.

FIG. 8 is a diagram of examples of the first influences and second influences calculated in the present embodiment. In the second embodiment, the influence of each component of the partial information N is considered, and thus a combination which increases its influence because some components are combined is emphasized, as illustrated in FIG. 8.

According to the present embodiment, the influence of an individual component is lightened, and the influence of a combination which increases its influence because some components are combined is emphasized through the consideration of the components of the partial information N. Accordingly, a piece of the partial information N that has a strong influence due to individual components is less likely to be selected, and thus, more appropriate information that has affected the derivation of the result of the inference can be presented to the doctor.

As described above, in step S3023 of the second embodiment, the first influence, in other words, the influence of each component of the partial information N is used to calculate the Nth influence. Alternatively, the Nth influence may be calculated by using the Nth-1 influence in place of the first influence. Alternatively, the Nth influence may be calculated by using the first to the Nth-1 influences. In such a way, an instance is emphasized where an influence upon the derivation of the result of the inference is small with a combination of up to N-1 components of the input information, but the influence upon the derivation of the result of the inference is increased with a combination of N components, where N represents the number of components. Thus, more appropriate information that has affected the derivation of the result of the inference can be presented to the doctor.

In the first and second embodiments, the first to the Nth influences are brought together to generate the information to be presented. Alternatively, information may be presented for each of the first to Nth influences. In this way, the user can make own judgment based on the information, allowing the doctor to obtain more appropriate information.

Alternatively, the present invention is achieved by executing the following processing. That is, software (a program) that achieves the functions of the embodiments described above is supplied through a network or a computer readable storage medium of various types to a system or a device, and a computer (alternatively, a CPU, MPU, or the like) of the system or the device reads the program to execute the processing.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)TM), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-189932, filed Aug. 30, 2012, which is hereby incorporated by reference herein in its entirety.

What is claimed is:

1. A diagnosis support system for presenting medical support information on a case, the system comprising:
    an inference unit configured to identify a diagnostic name of the case and obtain an inferred probability that medical information including a set having a plurality of elements has on identifying the diagnostic name of the case;

an acquisition unit configured to
  acquire an influence that each of first subsets contained in each of second subsets has with respect to the obtained inferred probability using a first function, and
  acquire an influence that each of the second subsets contained in the set has with respect to the obtained inferred probability using a second function which is different from the first function, wherein the each of the second subsets has a plurality of elements wherein the number of elements included in the second subset is larger than the number of elements included in the first subset;
a determination unit configured to determine a subset of the plurality of elements that is to be displayed, in accordance with (a) the influence of each of the first subsets and the influence of each of the second subsets and (b) an inclusion relationship between one of the first subsets and at least one of the second subsets to determine if one or more elements of the first subset are included in the second subset, wherein, if one or more elements of the first subset are included in the second subset, the determination unit determines the subset of the plurality of elements that is to be displayed in accordance with a comparing result between the influence of the first subset and the influence of the second subset; and
a display control unit configured to allow a display unit to display the identified diagnostic name and the determined subset.

2. The diagnosis support system according to claim 1, further comprising a selection unit configured to select a second subset among the second subsets contained in the set, wherein
the determination unit determines that, when a first subset among the first subsets contained in the second subset has an influence larger than the influence of the second subset, the first subset with the larger influence be displayed.

3. The diagnosis support system according to claim 2, wherein
the determination unit determines that the second subset should not be displayed.

4. The diagnosis support system according to claim 1, further comprising an instruction unit configured to instruct, in response to an operation input into an operation unit, the display control unit to allow the display unit to display the subset that has not determined as a subset to be displayed.

5. A medical diagnosis support device comprising:
an input unit configured to input medical information;
an inference unit configured to infer a probability of each diagnostic name from the medical information;
a first influence calculation unit configured to calculate a first influence of each component of the medical information upon a result of inference by the inference unit, wherein the first influence is calculated using a first function;
an Nth influence calculation unit configured to calculate an Nth influence of partial information of the medical information upon the result of the inference by the inference unit, the partial information comprising N components (N >1) of the medical information where N represents a number of the components, the Nth influence calculation unit is configured to calculated the Nth influence by taking into account a plurality of components included in the partial information, and wherein the Nth influence is calculated using a second function which is different from the first function; and
a generation unit configured to generate information to be presented to a user in accordance with a comparing result between the first influence of a particular component and the Nth influence, wherein the particular component is included in the N components.

6. The medical diagnosis support device according to claim 5, wherein the Nth influence calculation unit calculates the Nth influence by using the number N of components of the partial information.

7. The medical diagnosis support device according to claim 5, wherein the Nth influence calculation unit calculates the Nth influence by using the first influence.

8. The medical diagnosis support device according to claim 5, wherein the Nth influence calculation unit calculates the Nth influence by using an Nth-1 influence.

9. The medical diagnosis support device according to claim 5, wherein the generation unit selects, from each component of the medical information and the partial information of the medical information in consonance with a magnitude of the first to the Nth influences, information to be used for generating the information to be presented.

10. The medical diagnosis support device according to claim 9, wherein the generation unit does not select a piece of the partial information for generating the information to be presented when the Nth influence calculated for the partial information is smaller than an influence of at least one proper subset of the partial information.

11. The medical diagnosis support device according to claim 9, wherein the generation unit generates the information to be presented such that the information selected in consonance with the magnitude of the first to the Nth influences is presented as an inference reason for the result of the inference.

12. A medical diagnosis support method to be performed by a medical diagnosis support device, the method comprising:
inputting medical information;
inferring a probability of each diagnostic name from the medical information;
calculating a first influence of each component of the medical information upon a result of the inferring, wherein the first influence is calculated using a first function;
calculating an Nth influence of partial information of the medical information upon the result of the inferring, the partial information comprising N components (N>1) of the medical information where N represents a number of components, the Nth influence is calculated by taking into account a plurality of the components including in the each piece of partial information and the Nth influence is calculated using a second function which is different from the first function; and
generating information to be presented to a user in accordance with a comparing result between the first influence of a particular component and the Nth influence, wherein the particular component is included in the N components.

13. A method of processing medical support information on a case, the method comprising:
identifying a diagnostic name of the case and obtaining an inferred probability that medical information including a set having a plurality of elements has on identifying the diagnostic name of the case;
calculating an influence that each of first subsets contained in each of second subsets has with respect to the obtained inferred probability using a first function, and calculating an influence that each of the second subsets contained in the set has with respect to the obtained inferred probability using a second function which is different from the first function, wherein the each of the second subsets has a plurality of elements, wherein the number of elements included in the second subset is larger than the number of elements included in the first subset;

determining a subset of the plurality of elements that is to be displayed in accordance with (a) the influence of each of the first subsets and the influence of each of the second subsets and (b) an inclusion relationship between one of the first subsets and the at least one of the second subsets to determine if one or more elements of the first subset are included in the second subset, wherein, if one or more elements of the first subset are included in the second subset, the determination unit determines the subset of the plurality of elements that is to be displayed in accordance with a comparing result between the influence of the first subset and the influence of the second subset; and causing a display unit to display the identified diagnostic name and the determined subset.

14. A non-transitory computer readable storage medium storing instructions that, when executed by a computer, execute a method of processing medical support information on a case, the method comprising:

identifying a diagnostic name of the case and obtaining an inferred probability that medical information including a set having a plurality of elements has on identifying the diagnostic name of the case;

calculating an influence that of each of first subsets contained in each of second subsets has wit respect to the obtained inferred probability using a first function, and calculating an influence that of each of the second subsets contained in the set has with respect to the obtained inferred probability using a second function which is different from the first function, wherein the each of second subsets has a plurality of elements, wherein the number of elements included in the second subset is larger than the number of elements included in the first subset;

determining a subset of the plurality of elements that is to be displayed in accordance with (a) the influence of each of the first subsets and the influence of each of the second subsets and (b) an inclusion relationship between one of the first subsets and the at least one of the second subsets to determine if one or more elements of the first subset are included in the second subset, wherein, if one or more elements of the first subset are included in the second subset, the determination unit determines the subset of the plurality of elements that is to be displayed in accordance with a comparing result between the influence of the first subset and the influence of the second subset; and causing a display unit to display the identified diagnostic name and the determined subset.

15. The diagnosis support system according to claim 1, wherein each of the first subsets has only one element.

16. The diagnosis support system according to claim 15, wherein the determination unit determines that, when (1) a first subset among the first subsets has an influence larger than the influence of a second subset among the second subsets and (2) the first subset having the influence larger than the influence of the second subset is included in the second subset, the first subset with the larger influence be displayed and the second subset with the smaller influence not be displayed.

17. The diagnosis support system according to claim 1, wherein the second function includes a term which prevents the influence of each of first subsets from increasing and the term is not included in the first function.

18. A diagnosis support system for presenting medical support information on a case, the system comprising:

an inference unit configured to identify a diagnostic name of the case and obtain an inferred probability that medical information including a set having a plurality of elements has on identifying the diagnostic name of the case;

an acquisition unit configured to acquire an influence that a first subset contained in a second subset has with respect to the obtained inferred probability using a first function, and acquire an influence that the second subset contained in the set has with respect to the obtained inferred probability using a second function which is different from the first function, wherein the second subset has a plurality of elements wherein the number of elements included in the second subset is larger than the number of elements included in the first subset;

a determination unit configured to determine a subset of the plurality of elements that is to be displayed, in accordance with (a) the influence of the first subset and the influence of the second subset and (b) an inclusion relationship between the first subset and the second subset to determine if one or more elements of the first subset are included in the second subset, wherein, if one or more elements of the first subset are included in the second subset, the determination unit determines the subset of the plurality of elements that is to be displayed in accordance with a comparing result between the influence of the first subset and the influence of the second subset; and a display control unit configured to allow a display unit to display the identified diagnostic name and the determined subset.

* * * * *